(12) United States Patent
    Krueger

(10) Patent No.: US 10,830,842 B2
(45) Date of Patent: Nov. 10, 2020

(54) METHOD FOR DEVICE LOCALIZATION USING MAGNETIC RESONANCE IMAGING

(71) Applicant: KONINKLIJKE PHILIPS N.V., Eindhoven (NL)

(72) Inventor: Sascha Krueger, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 192 days.

(21) Appl. No.: 15/763,469

(22) PCT Filed: Sep. 29, 2016

(86) PCT No.: PCT/EP2016/073160
§ 371 (c)(1),
(2) Date: Mar. 27, 2018

(87) PCT Pub. No.: WO2017/055380
PCT Pub. Date: Apr. 6, 2017

(65) Prior Publication Data
US 2018/0292475 A1    Oct. 11, 2018

(30) Foreign Application Priority Data
Sep. 30, 2015    (EP) .................................... 15187556

(51) Int. Cl.
    *G01R 33/28*    (2006.01)
    *A61B 5/055*    (2006.01)
    (Continued)

(52) U.S. Cl.
    CPC ............ *G01R 33/286* (2013.01); *A61B 5/055* (2013.01); *A61B 5/062* (2013.01); *A61B 5/748* (2013.01);
    (Continued)

(58) Field of Classification Search
    None
    See application file for complete search history.

(56) References Cited

U.S. PATENT DOCUMENTS 5,307,808 A    5/1994    Dumoulin et al.
5,565,412 A    10/1996   Hennig
(Continued)

OTHER PUBLICATIONS

Fischbach, F. et al "MR Guided Freehand Biopsy of Breast Lesions in a 1.0 T Open MR Imager With Near Real Time Interactive Platform . . ." Radiology, 2012, 265(2) p. 359-370.
(Continued)

*Primary Examiner* — Paresh Patel
(74) *Attorney, Agent, or Firm* — Sherry Austin

(57) ABSTRACT

It is an object of the invention to provide for an improved method for device localization using magnetic resonance imaging (MRI) during MRI guided interventions. This object is achieved by a method for device localization using magnetic resonance imaging (MRI) from a region of interest during an MRI guided intervention, wherein the method comprises the following steps: acquiring magnetic resonance data from the region of interest and reconstructing a biplane image, representing two intersecting slices, wherein an image contrast of the biplane image is such that it is suitable for device localization and wherein a thickness of the slices is such that the slices substantially cover the region of interest and; detecting a device location and orientation in both slices and; acquiring magnetic resonance data from a third slice comprising at least part of the region of interest and reconstructing an anatomical image thereof, wherein the image contrast of the anatomical image is such that it is suitable for identifying an anatomical structure of interest, wherein a thickness of the third slice is smaller than the thickness of the biplane slices.

19 Claims, 3 Drawing Sheets

(51) Int. Cl.
  *A61B 5/06* (2006.01)
  *A61B 34/20* (2016.01)
  *A61B 5/00* (2006.01)

(52) U.S. Cl.
  CPC ...... *A61B 34/20* (2016.02); *A61B 2034/2051* (2016.02); *A61B 2034/2065* (2016.02); *A61B 2576/00* (2013.01)

(56) References Cited

U.S. PATENT DOCUMENTS

| | | | |
|---|---|---|---|
| 6,459,264 | B1 | 10/2002 | Fain et al. |
| 8,369,930 | B2 | 2/2013 | Jenkins et al. |
| 2005/0079636 | A1* | 4/2005 | White ................ A61B 5/4076 436/518 |
| 2007/0249934 | A1 | 10/2007 | Aksit et al. |
| 2008/0097189 | A1 | 4/2008 | Dumoulin et al. |
| 2008/0114235 | A1 | 5/2008 | Unal et al. |
| 2010/0312096 | A1 | 12/2010 | Guttman et al. |

OTHER PUBLICATIONS

Ashvin K. George et al: "Visualization of active devices and automatic slice repositioning ("SnapTo") for MRI-guided interventions",Magnetic Resonance in Medicine.,vol. 63, No. 4, Apr. 1, 2010 (Apr. 1, 2010), pp. 1070-1079.

Susanne C Göhde et al: "MR-Guided Cholecystostomy: Assessment of Biplanar,Real-Time Needle Tracking in Three Pigs",Cardiovasc Intervent Radiol, Jan. 1, 1997 (Jan. 1, 1997), pp. 295-299.

Hahn T et al: "Fast 3D tracking of 19F labeled small capsules for combined morphology and real-time flow studies in the gastrointestinal tract".Proceedings of the International Society for Magnetic Resonance in Meoicine, ISMRM, 18TH Scientific Meeting and Exhibition,Stockholm, Sweden, May 1-7, 2010, Apr. 17, 2010 (Apr. 17, 2010), p. 5360.

Garnov Nikita et al: "Suitability of miniature inductively coupled RF coils as MR-visible markers for clinical purposes". Medical Physics, AIP, Melville, NY, US,vol. 38, No. 11, Nov. 1, 2011 (Nov. 1, 2011), pp. 6327-6335.

\* cited by examiner

METHOD FOR DEVICE LOCALIZATION USING MAGNETIC RESONANCE IMAGING

CROSS REFERENCE TO RELATED APPLICATIONS

This application is a U.S. national phase application of International Application No. PCT/EP2016/073160, filed on Sep. 29, 2016, which claims the benefit of EP Application Serial No. 15187556.4 filed on Sep. 30, 2015 and is incorporated herein by reference.

FIELD OF THE INVENTION

The invention relates to the field of magnetic resonance imaging and more specifically to the field of magnetic resonance imaging guided interventions.

BACKGROUND OF THE INVENTION

Magnetic resonance imaging (MRI) could be used for device localization during MRI guided interventions. Such interventions could for example be biopsy procedures or MRI electrophysiology. Robust automated full-shape device localization in MRI is a challenging task. One way of performing device localization is by means of active tracking. Active tracking is often limited to track a limited number of points on the device tip. Because of its dependence on local coils, which may break, this method may malfunction, making the device unlocalizable amidst a procedure.

Another way of performing device localization is by means of imaging based or passive localization. Imaging based device localization is described in Fischbach, F et al, MR-guided freehand biopsy of breast lesions in a 1.0-T open MR imager with a near-real-time interactive platform: preliminary experience, Radiology 2012; 265(2): 359-370. Imaging-based (passive) localization of a device solves the above described issues of active tracking but often makes it necessary to make a compromise between optimal delineation of anatomical detail in thin slices and robust and fast localization of slices with a sufficiently large artifact. To capture the device in full shape, the slices also are typically thicker which additionally compromises the anatomical detail.

SUMMARY OF THE INVENTION

It is an object of the invention to provide for an improved method for device localization using magnetic resonance imaging (MRI) during MRI guided interventions. This object is achieved by a method for device localization from a region of interest using magnetic resonance imaging (MRI) during an MRI guided intervention, wherein the method comprises the following steps:

acquiring magnetic resonance data from the region of interest and reconstructing a biplane image, representing two intersecting slices, wherein an image contrast of the biplane image is such that it is suitable for device localization and wherein a thickness of the slices is such that the slices substantially cover the region of interest, wherein the slices are selected by application of temporary slice encoding gradient and;

detecting a device location and orientation in both slices and;

acquiring magnetic resonance data from a third slice comprising at least part of the region of interest and reconstructing an anatomical image thereof, wherein the image contrast of the anatomical image is such that it is suitable for identifying an anatomical structure of interest, wherein a thickness of the third slice is smaller than the thickness of the biplane slices.

This object is also achieved by an MRI system according to claim 9 and a computer program product according to claim 10.

Because two different kinds of images are used (biplane and anatomical image) no compromise has to be made in the contrast of the images. The contrast in the biplane image is preferably optimized for device localization, whereas the contrast in the anatomical image is preferably optimized such that it is suitable for identifying one or more anatomical structures of interest. In other words the contrast in the biplane image is different than in the anatomical image. Such structures could for example be a pathological condition (e.g. a tumor, stenosis) or organ or tissue borders. Further, because the device is localized by means of the biplane image having thick slices, a thickness of the anatomical image slice can be small, which will likely improve the detectability of anatomical details. Therefore, the invention provides for a method of improved device localization.

A region of interest could for example be a human heart or prosate. Also it could be just a part of an anatomy. In those cases the region of interest could for example comprise a structure of risk and a target location. The thickness of the biplane slices is preferably such that more than 50% of the region of interest is covered by the biplane image. More prefereably, 70% of the region of interest is covered by the biplane image, more preferably over 80% of the region of interest is covered by the biplane, more preferably over 90% of the region of interest is covered by the biplane image and most preferably the region of interest is fully covered by the biplane image. It should be noted that although the biplane slices are thick with respect to the region of interest, the biplane slices do have a finite thickness and they are selected by means of a slice encoding gradient. Preferably, the slice thickness of the biplane slices is about the same size as the region of interest or smaller, because this will make the device detection and localization much more robust compared to a larger slice thickness. Also the extent of the anatomical image is preferably similar or smaller than the region of interest. In this way, the acquired anatomical image will be easier to interpret by the operator.

The biplane comprises two intersecting slices. Preferably these two slices are substantially orthogonal to each other.

According to embodiments of the invention, the biplane image is used to guide the device roughly to the structure of interest. The target location (e.g. a pathological condition) is comprised in the anatomical image. The location of the target location can be derived from the anatomical image and the location of the third slice. When the device is in the neighbourhood of the target location, the anatomical image can be used to guide the device exactly to the target location. This could for example be advantageous during MRI guided prostate biopsy. A first part of a trajectory of a device (in this case a biopsy needle) goes through tissues like muscles and fat. To guide the needle through these tissues a balanced sequence suffices. Such a sequence helps to visualize the needle and some vessels, but it may also show an outline of the prostate. After the needle has entered the prostate, the anatomical image may be updated more frequently. For prostate for example T2w Turbo Spin Echo (TSE) may be used to acquire and update the anatomical image.

In a preferred embodiment, the position and orientation of the third slide is derived from the location and orientation of the device detected in the biplane slices. In this way, a functional part of the device is substantially comprised within the third slice. Such functional part could be anything that is used to perform the real intervention. Often the functional part is located at a tip of the device. Examples of functional parts are a biopsy forceps, or a part of the device that emits energy for example for ablation of tissue. From the data acquired from the third slice, the anatomical image is reconstructed. So, the functional part of the device is substantially comprised in the anatomical image. Preferably, the functional part of the device is comprised for more than 50% within the anatomical image, more preferably the functional part of the device is comprised for more than 70% within the anatomical image, even more preferably the functional part of the device is comprised for more than 90% within the anatomical image. This embodiment is advantageous, because in this way it can be monitored better if the device is about to enter an anatomical region or structure that should be avoided.

MRI sequences which result in an image contrast suitable for device localization are well known in the field of MRI, especially in the field of MRI guided interventions. Examples of sequences resulting in images suitable for device localization are balanced sequences or gradient echo sequences. A frame rate used to update the biplane image will depend on the anatomy of interest. Some anatomies, e.g. like liver mainly move due to breathing. For such anatomies a frame rate of about 1 Hz is sufficient. For interventions on the spine this frame rate can be lower. For cardiac intervention one may think of a frame rate of about 5-10 Hz. Similarly, MRI sequences which result in an image contrast suitable for identifying an anatomical structure of interest are also well known in the art. Examples of such sequences are T2w TSE, inflow enhanced angiography sequences, sequences used for dark blood magnetic resonance angiography, but also sequences resulting in a more functional contrast like sequences for diffusion weighted imaging.

According to an embodiment of the invention, multiple biplane images and multiple anatomical images are acquired and the acquisition of the biplanes images is interleaved with the acquisition of the anatomical images. This embodiment is advantageous, because hereby each time the biplane image can be used to localize the device and to determine the position and orientation of the third slice such that the device is comprised in the region from which the anatomical image is acquired. According to an advantageous embodiment of the invention, the anatomical images are only updated when needed, e.g. if the device is no longer comprised within third slice. This embodiment is especially advantageous if the location and orientation of the device are projected from the biplane image to the anatomical image, as will be discussed below. This embodiment is advantageous for tracking the device and for guidance of the device to the target location.

According to an embodiment of the invention the position and orientation of the third slice is determined automatically based on an automatic detection of the device location and orientation from the biplane image. This embodiment is advantageous, because it may make the method more time efficient. Further, it may allow an operator of the system to focus more on guiding the device to the right location instead of taking care that the image orientation of the third slice is as desired.

According to a further embodiment of the invention the device location and orientation are manually detected. This embodiment is advantageous, because it may be safer.

According to a further embodiment of the invention, the location and orientation of the device retrieved from the biplane image are shown as a projection on the anatomical image. This is advantageous, because in this way the device can be seen relative to the anatomical image, while no compromise in image contrast is needed in the anatomical image.

According to further embodiments of the invention, the device is localized by alignment of a location where the intersecting slices overlap with a representation of the device in the biplane image. This is advantageous, because this makes the method is more intuitive and easier to use for the user. A most simple implementation is to place the third slice at the position of the device, i.e. at a signal (void) caused by the device visible in both the intersecting biplane images. In a preferred embodiment an operator will continuously adapt the position of the third image and along with that also those of the biplane slices (due to the slab thickness this does not compromise device capture) with the task to align the third image with the signal from the device in the at least two thick slabs. This can be supported by computer algorithms localizing the device signal/void in the individual thick slab images but the actual localization with respect to the anatomy will still be fully image-based.

These and other aspects of the invention will be apparent from and elucidated with reference to the embodiments described hereinafter.

DETAILED DESCRIPTION OF THE INVENTION

Figure 1:
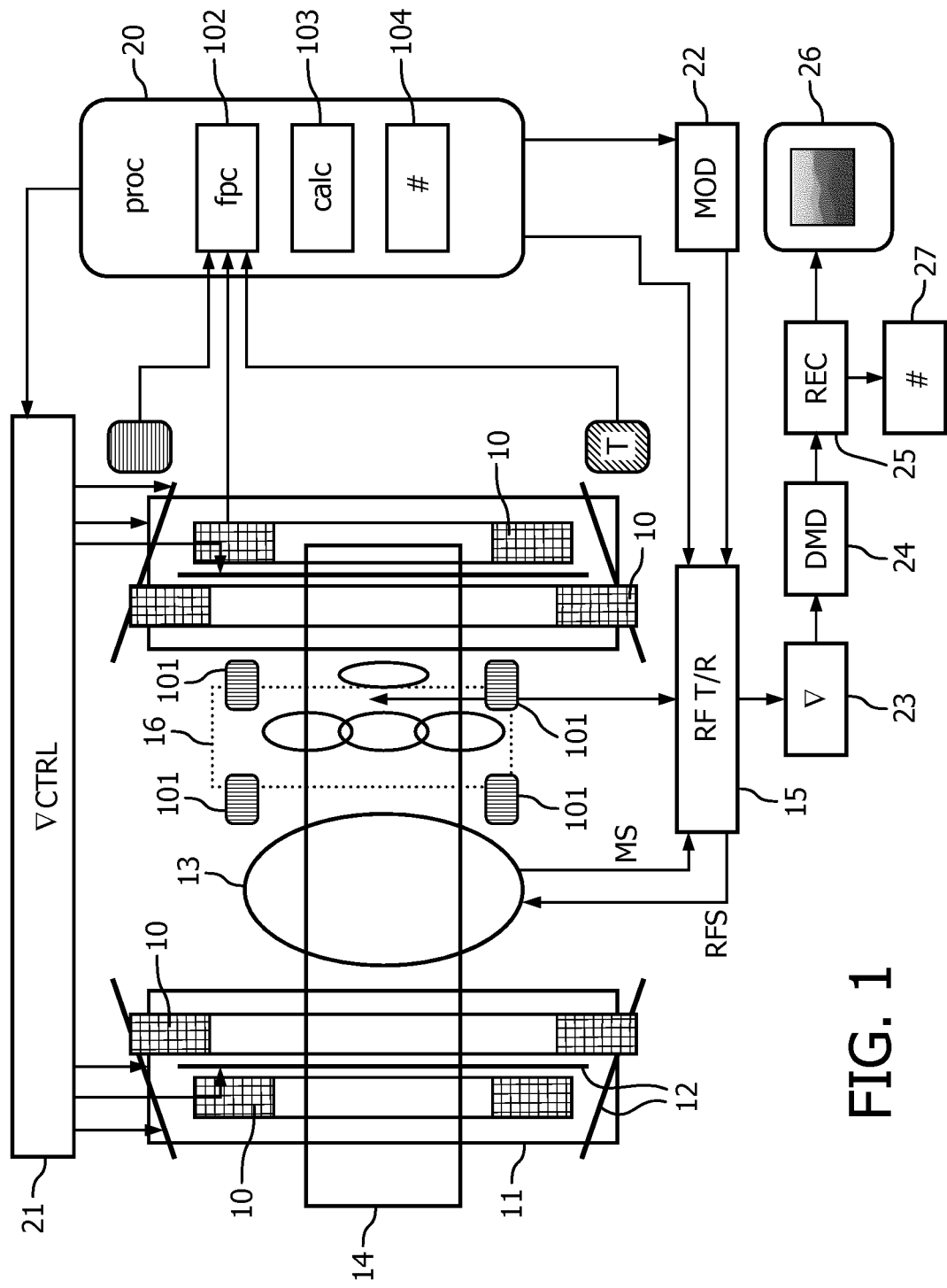
FIG. 1 shows diagrammatically a magnetic resonance imaging system in which an embodiment of the invention is used and FIG. 2 shows a biplane image acquired using a method according to embodiments of the invention and FIG. 3 shows anatomical images acquired using a method according to embodiments of the invention.

FIG. 1 shows diagrammatically a magnetic resonance imaging system in which an embodiment of the invention is used. The magnetic resonance imaging system includes a main magnet with a set of main coils 10 whereby the steady, uniform magnetic field is generated. The main coils are constructed, for example in such a manner that they from a bore to enclose a tunnel-shaped examination space. The patient to be examined is placed on a patient carrier which is slid into this tunnel-shaped examination space. The magnetic resonance imaging system also includes a number of gradient coils 11, 12 whereby magnetic fields exhibiting spatial variations, notably in the form of temporary gradients in individual directions, are generated so as to be superposed on the uniform magnetic field. The gradient coils 11, 12 are connected to a gradient control 21 which includes one or more gradient amplifier and a controllable power supply unit. The gradient coils 11, 12 are energised by application of an electric current by means of the power supply unit 21; to this end the power supply unit is fitted with electronic gradient amplification circuit that applies the electric current to the gradient coils so as to generate gradient pulses (also termed 'gradient waveforms') of appropriate temporal shape. The strength, direction and duration of the gradients are controlled by control of the power supply unit. The magnetic resonance imaging system also includes transmission and receiving antennae (coils or coil arrays) 13, 16 for generating the RF excitation pulses and for picking up the magnetic resonance signals, respectively. The transmission coil 13 is preferably constructed as a body coil 13 whereby (a part of) the object to be examined can be enclosed. The body coil is usually arranged in the magnetic resonance imaging system in such a manner that the patient 30 to be examined is enclosed by the body coil 13 when he or she is arranged in the magnetic resonance imaging system. The body coil 13 acts as a transmission antenna for the transmission of the RF excitation pulses and RF refocusing pulses. Preferably, the body coil 13 involves a spatially uniform intensity distribution of the transmitted RF pulses (RFS). The same coil or antenna is generally used alternately as the transmission coil and the receiving coil. Typically, a receiving coil includes a multiplicity of elements, each typically forming a single loop. Various geometries of the shape of the loop and the arrangement of various elements are possible The transmission and receiving coil 13 is connected to an electronic transmission and receiving circuit 15.

It is to be noted that is that there is one (or a few) RF antenna elements that can act as transmit and receive; additionally, typically, the user may choose to employ an application-specific receive antenna that typically is formed as an array of receive-elements. For example, surface coil arrays 16 can be used as receiving and/or transmission coils. Such surface coil arrays have a high sensitivity in a comparatively small volume. The receiving coil is connected to a preamplifier 23. The preamplifier 23 amplifies the RF resonance signal (MS) received by the receiving coil 16 and the amplified RF resonance signal is applied to a demodulator 24. The receiving antennae, such as the surface coil arrays, are connected to a demodulator 24 and the received pre-amplified magnetic resonance signals (MS) are demodulated by means of the demodulator 24. The pre-amplifier 23 and demodulator 24 may be digitally implemented and integrated in the surface coil array The demodulated magnetic resonance signals (DMS) are applied to a reconstruction unit. The demodulator 24 demodulates the amplified RF resonance signal. The demodulated resonance signal contains the actual information concerning the local spin densities in the part of the object to be imaged. Furthermore, the transmission and receiving circuit 15 is connected to a modulator 22. The modulator 22 and the transmission and receiving circuit 15 activate the transmission coil 13 so as to transmit the RF excitation and refocusing pulses. In particular the surface receive coil arrays 16 are coupled to the transmission and receive circuit by way of a wireless link. Magnetic resonance signal data received by the surface coil arrays 16 are transmitted to the transmission and receiving circuit 15 and control signals (e.g. to tune and detune the surface coils) are sent to the surface coils over the wireless link.

The reconstruction unit derives one or more image signals from the demodulated magnetic resonance signals (DMS), which image signals represent the image information of the imaged part of the object to be examined. The reconstruction unit 25 in practice is constructed preferably as a digital image processing unit 25 which is programmed so as to derive from the demodulated magnetic resonance signals the image signals which represent the image information of the part of the object to be imaged. The signal on the output of the reconstruction is applied to a monitor 26, so that the reconstructed magnetic resonance image can be displayed on the monitor. It is alternatively possible to store the signal from the reconstruction unit 25 in a buffer unit 27 while awaiting further processing or display.

The magnetic resonance imaging system according to the invention is also provided with a control unit 20, for example in the form of a computer which includes a (micro) processor. The control unit 20 controls the execution of the RF excitations and the application of the temporary gradient fields. To this end, the computer program according to the invention is loaded, for example, into the control unit 20 and the reconstruction unit 25.

Figure 2:
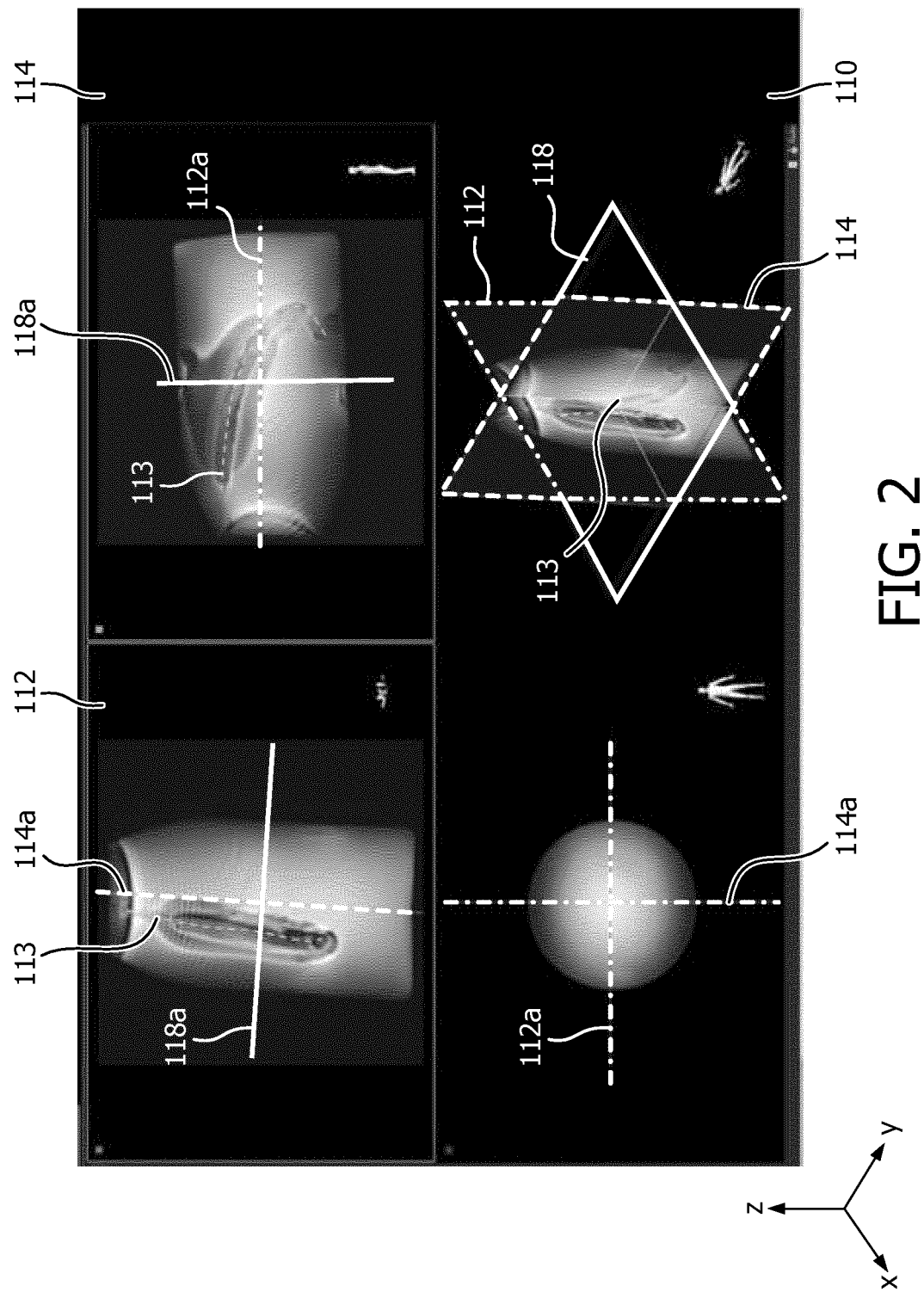

FIG. 2 shows a biplane image acquired using a method according to embodiments of the invention The biplane image 110 comprises two orthogonal slices 112, 114. The slices are thick compared to the region or anatomy of interest, such that an artifact 113 caused by the device is always captured as long as it is within the region or anatomy of interest. Because the slices are that thick a single slice cannot be used to determine the exact position and orientation in the direction of the thickness of the slice. For example, slice 112 can be used to determine the direction and orientation of device in the x and z direction, but not in the y-direction. However, the position and orientation of device 113 on the y-axis or in the y-direction can be determined from slice 114. This information is used to determine the position and orientation the third slice. As can be seen in FIG. 2, the device 113 is not in the center of the biplane image. To address this an operator of the system could move slice 114 (or line 114a in the left upper image), such that it is aligned with the artifact 113 caused by the device. Additionally, he could move slice 112 (or line 112a in the upper right image) such that is aligned with the artifact 113. If such manipulation is performed by the operator, this is an indication that the device has moved outside the anatomical image and that the anatomical image should be updated. This update could be triggered automatically.

Figure 3:
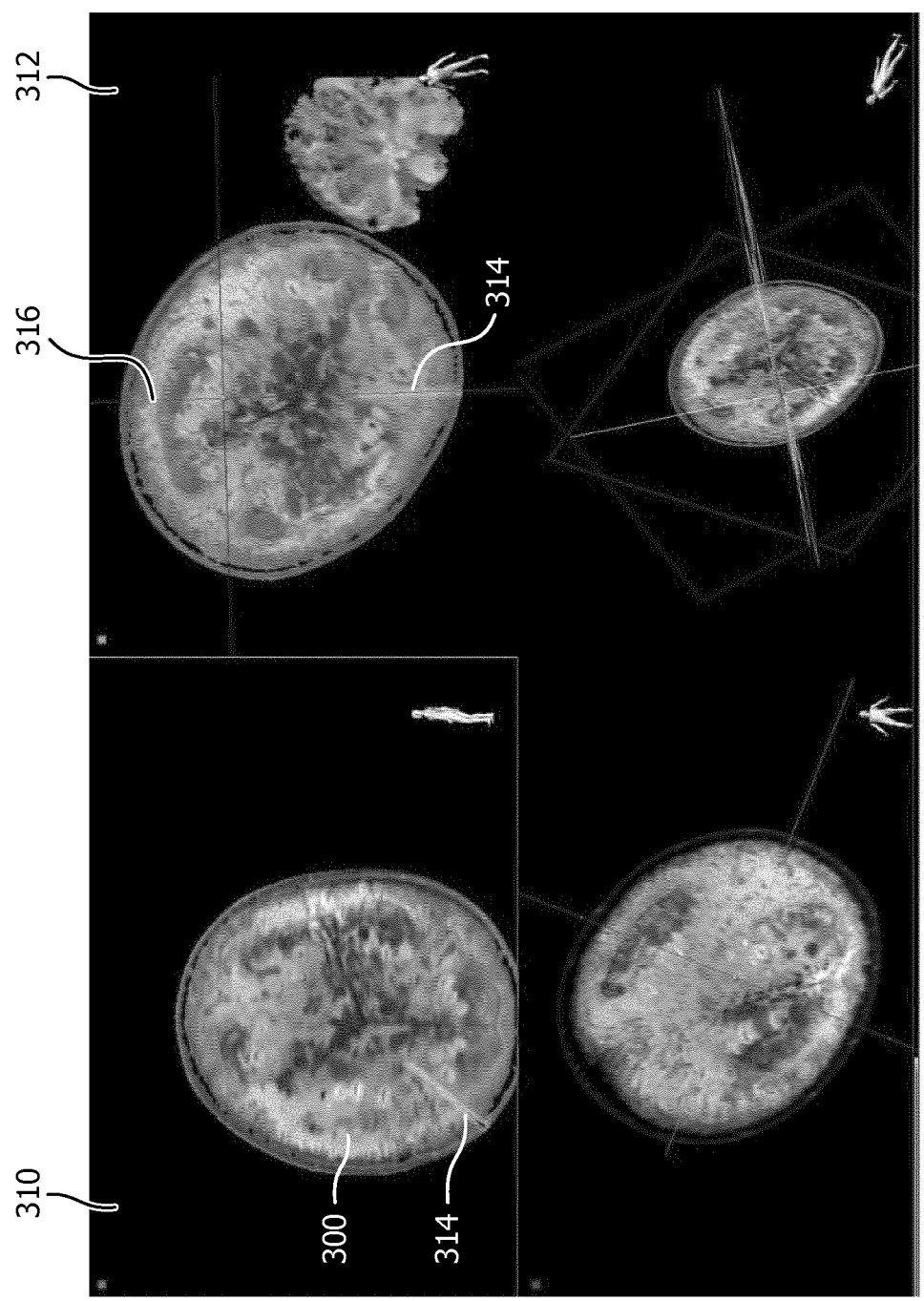

FIG. 3 shows anatomical images 310, 312 acquired using a method according to embodiments of the invention. The anatomical images show a representation of a melon 300. A representation 314 of a device, in this case a needle is retrieved from the biplane image and projected on top of the anatomical images. From anatomical image 310 it is not clear if the device is within the region from which anatomical image 310 is acquired, or whether the device is in fact below or above this region. Whether the device is within the region from which anatomical image 310 is acquired can be determined from anatomical image 312, which is an image acquired with another orientation, in this case orthogonal to anatomical image 310. Line 316 in anatomical image 312, shows the position and orientation of anatomical image 310. The device is within the region from which anatomical image 310 is acquired, as long as the projection of the device 314 overlaps line 316.

Whilst the invention has been illustrated and described in detail in the drawings and foregoing description, such illustrations and description are to be considered illustrative or exemplary and not restrictive; the invention is not limited to the disclosed embodiments.

The invention claimed is:

1. A method for device localization from a region of interest using magnetic resonance imaging (MRI) during an MRI guided intervention, wherein the method comprises the following steps:
   acquiring magnetic resonance data from the region of interest and reconstructing a biplane image, representing two intersecting slices, wherein an image contrast of the biplane image is such that it is suitable for device localization and wherein a thickness of the slices is such that the slices substantially cover the region of interest, wherein the slices are selected by application of temporary slice encoding gradient;

detecting a device location and orientation in both slices; and acquiring magnetic resonance data from a third slice comprising at least part of the region of interest and reconstructing an anatomical image thereof, wherein the image contrast of the anatomical image is such that it is suitable for identifying an anatomical structure of interest, wherein a thickness of the third slice is smaller than the thickness of the biplane slices, thereby optimizing the contrast in the biplane image for device localization and the contrast in the anatomical image for identifying the anatomical structure of interest.

2. A method for device localization as claimed in claim 1, wherein the alignment of the location where the intersecting slices overlap with the representation of the device in the biplane image triggers a geometry update of the third slice, such that at least part of the representation of the device is within the plane of the third slice.

3. A method for device localization as claimed in claim 1, wherein a position and orientation of the third slice is derived from the location and orientation of the device detected in the biplane slices such that a functional part of the device is substantially comprised in a region from which the anatomical image is acquired.

4. A method for device localization as claimed in claim 1, wherein multiple biplane images and multiple anatomical images are acquired and wherein the acquisition of the biplanes images is interleaved with the acquisition of the anatomical images.

5. A method for device localization as claimed in claim 1, wherein the location and orientation of the device retrieved from the biplane image are shown as a projection on the anatomical image.

6. A method for device localization as claimed in claim 1, wherein the contrast in the anatomical image is such that it is suitable for device detection.

7. A magnetic resonance imaging system configured to be used for performing the method in claim 1.

8. A computer program product comprising program code for causing a computer to control a magnetic resonance imaging system to carry out the steps of the method in claim 1.

9. The method of claim 1, wherein the device is localized by alignment of a location where the intersecting slices overlap with a representation of the device in the biplane image, wherein the device location and orientation are manually detected.

10. The magnetic resonance imaging system of claim 7, wherein the alignment of the location where the intersecting slices overlap with the representation of the device in the biplane image triggers a geometry update of the third slice, such that at least part of the representation of the device is within the plane of the third slice.

11. The magnetic resonance imaging system of claim 7, wherein a position and orientation of the third slice is derived from the location and orientation of the device detected in the biplane slices such that a functional part of the device is substantially comprised in a region from which the anatomical image is acquired.

12. The magnetic resonance imaging system of claim 7, wherein multiple biplane images and multiple anatomical images are acquired and wherein the acquisition of the biplanes images is interleaved with the acquisition of the anatomical images.

13. The magnetic resonance imaging system of claim 7, wherein the location and orientation of the device retrieved from the biplane image are shown as a projection on the anatomical image.

14. The magnetic resonance imaging system of claim 7, wherein the contrast in the anatomical image is such that it is suitable for device detection.

15. The computer program product of claim 8, wherein the alignment of the location where the intersecting slices overlap with the representation of the device in the biplane image triggers a geometry update of the third slice, such that at least part of the representation of the device is within the plane of the third slice.

16. The computer program product of claim 8, wherein a position and orientation of the third slice is derived from the location and orientation of the device detected in the biplane slices such that a functional part of the device is substantially comprised in a region from which the anatomical image is acquired.

17. The computer program product of claim 8, wherein multiple biplane images and multiple anatomical images are acquired and wherein the acquisition of the biplanes images is interleaved with the acquisition of the anatomical images.

18. The computer program product of claim 8, wherein the location and orientation of the device retrieved from the biplane image are shown as a projection on the anatomical image.

19. The computer program product of claim 8, wherein the contrast in the anatomical image is such that it is suitable for device detection.

* * * * *